(12) United States Patent
Serra et al.

(10) Patent No.: US 7,419,931 B2
(45) Date of Patent: Sep. 2, 2008

(54) CATALYST COMPRISING A 10MR ZEOLITE AND A 12MR ZEOLITE, AND ITS USE IN TRANSALKYLATION OF ALKYLAROMATIC HYDROCARBONS

(75) Inventors: José Manuel Serra, Valencia (ES); Avelino Corma, Valence (ES); Emmanuelle Guillon, Saint Genis Laval (FR)

(73) Assignee: Institute Francais du Petrole, Rueil Malmaison Cedex (FR)

( * ) Notice: Subject to any disclaimer, the term of this patent is extended or adjusted under 35 U.S.C. 154(b) by 516 days.

(21) Appl. No.: 11/104,622

(22) Filed: Apr. 13, 2005

(65) Prior Publication Data

US 2005/0234279 A1   Oct. 20, 2005

(30) Foreign Application Priority Data

Apr. 14, 2004   (FR) .................................. 04 03887

(51) Int. Cl.
| | |
|---|---|
| *B01J 29/04* | (2006.01) |
| *B01J 29/18* | (2006.01) |
| *B01J 29/076* | (2006.01) |
| *B01J 29/26* | (2006.01) |
| *C07C 15/02* | (2006.01) |
| *C07C 15/067* | (2006.01) |
| *C07C 15/08* | (2006.01) |

(52) U.S. Cl. ............................. 502/64; 502/67; 502/68; 502/71; 502/77; 502/78; 585/475

(58) Field of Classification Search ................... 502/64, 502/67, 68, 71, 77, 78; 585/475
See application file for complete search history.

(56) References Cited

U.S. PATENT DOCUMENTS

| 5,759,950 | A | 6/1998 | Gui et al. |
| 5,800,698 | A | 9/1998 | Tejada et al. |
| 6,344,135 | B1 | 2/2002 | Benazzi et al. |
| 6,613,709 | B1 | 9/2003 | Merlen et al. |

FOREIGN PATENT DOCUMENTS

| EP | 1077083 A | 2/2001 |
| FR | 2790001 A | 8/2000 |
| WO | WO 00/38834 A | 7/2000 |
| WO | WO 2004/046278 A1 | 6/2004 |

*Primary Examiner*—Elizabeth D. Wood
(74) *Attorney, Agent, or Firm*—Millen, White, Zelano & Branigan, P.C.

(57) ABSTRACT

A catalyst is described which comprises at least one zeolite with channels with openings defined by a ring having 10 oxygen atoms (10 MI), at least one zeolite with at least channels or side pockets with openings defined by a ring having 12 oxygen atoms (12 MR), at least one metal selected from the group constituted by group IIIA and VIIB metals and at least one porous mineral matrix. Said catalyst optionally also contains at least one metal selected from the group constituted by group IVA and VIB metals. The catalyst of the invention is used in a process for the transalkylation of alkylaromatic hydrocarbons such as toluene or benzene and alkylaromatics containing at least 9 carbon atoms.

20 Claims, No Drawings

CATALYST COMPRISING A 10MR ZEOLITE AND A 12MR ZEOLITE, AND ITS USE IN TRANSALKYLATION OF ALKYLAROMATIC HYDROCARBONS

TECHNICAL FIELD

The present invention relates to a catalyst for use, for example, in reactions for transforming aromatic hydrocarbons. More precisely, it relates to a catalyst for transalkylation of alkylaromatic hydrocarbons, and preferably for the transalkylation of benzene or toluene and aromatic compounds containing at least 9 carbon atoms, to produce xylenes. The present invention also relates to the preparation of said catalyst and to its use in a process for the transalkylation of alkylaromatic hydrocarbons.

PRIOR ART

Many catalysts for disproportionation and/or transalkylation have already been described in the prior art, and are based on mordenite. (United States patents U.S. Pat. No. 3,506,731, U.S. Pat. No. 4,151,120, U.S. Pat. No. 4,180,693, U.S. Pat. No. 4,210,770, U.S. Pat. No. 3,281,483, U.S. Pat. No. 3,780, 121 or U.S. Pat. No. 3,629,351 or based on omega zeolite (U.S. Pat. No. 5,210,356, U.S. Pat. No. 5,371,311).

European patent application EP-A1-0 731 071 describes the use of a catalyst based on mordenite zeolite and a metal (Re, Ni, Co, Mo, Cr, W) for transalkylation of aromatic C9 cuts containing an aromatic containing at least one ethyl group.

French patent application FR-A-2 744 650 describes the use of a composite catalyst for the disproportionation/transalkylation of alkylaromatic hydrocarbons based on zeolite with a mordenite structure type and a mazzite structure type.

U.S. Pat. No. 5,942,651 describes a catalytic system comprising two distinct and separate catalytic compositions, one based on zeolite having a constraint index in the range 0.5 to 3 and a noble metal and the second based on zeolite having a constraint index in the range 3 to 12 with no added metal. U.S. Pat. No. 5,905,051 discloses a catalytic system comprising a first catalytic composition based on beta zeolite promoted by a metal and a second catalytic composition based on ZSM-5 zeolite into which a promoter (S, P, Si) has been impregnated. The catalytic systems disclosed in those documents are used in a process for converting aromatic compounds comprising at least 9 carbon atoms per molecule.

SUMMARY

The present invention concerns a catalyst comprising at least one zeolite with channels with openings defined by a ring having 10 oxygen atoms (10 MI), at least one zeolite with at least channels or side pockets with openings defined by a ring having 12 oxygen atoms (12 MI), at least one metal selected from the group constituted by group IIIA and VIIB metals and at least one porous mineral matrix. The catalyst of the present invention also optionally comprises at least one metal selected from the group constituted by group IVA and VIB metals. Each of the zeolites included in the catalyst of the invention contains silicon and at least one element T selected from the group formed by aluminium, iron, gallium and boron. The catalyst of the present invention is free from any group VIII metal.

The present invention also concerns the use of said catalyst in a process for the transalkylation of alkylaromatic hydrocarbons such as toluene and alkylaromatics containing at least 9 carbon atoms or benzene and alkylaromatics containing at least 9 carbon atoms. In particular, said catalyst is very powerful when processing C9+ aromatic feeds containing a percentage of aromatic molecules containing at least 10 carbon atoms and more of more than 5% by weight, said feed also possibly containing benzene.

ADVANTAGE

Surprisingly, it has been discovered that a composite catalyst comprising an association of at least one zeolite with channels with openings defined by a ring having 10 oxygen atoms (10 MI) and at least one zeolite with at least channels or side pockets with openings defined by a ring having 12 oxygen atoms (12 MI), and at least one metal selected from the group constituted by group IIIA and VIIB metals results in improved catalytic performances, in particular as regards activity, stability and selectivity, in the disproportionation of alkylaromatic hydrocarbons such as toluene or benzene and/ or in reactions for transalkylation of alkylaromatic hydrocarbons such as toluene, benzene and trimethylbenzeenes or alkylaromatics containing more than 9 carbon atoms (C9+). The catalyst of the invention is very powerful in the treatment of C9+ aromatic feeds containing a high percentage (more than 5% by weight) of aromatic molecules containing 10 carbon atoms and more, which means that heavy molecules, for example dimethylethylbenzenes or diethylbenzenes, generally having alkyl groups containing more than one carbon atom (ethyl, propyl, etc), can be upgraded to xylenes. When used in a process for the transalkylation of benzene or toluene and alkylaromatic compounds, the catalyst of the invention can considerably improve the benzene and xylene yields obtained, which products have a high added value compared with the yields obtained with known prior art catalysts.

Further, by adjusting the relative quantity of the two zeolites, the 10 MI zeolite and that with at least 12 MI, in the catalyst of the invention, it is possible to treat a very wide range of mixtures of hydrocarbon feeds.

DESCRIPTION

The present invention concerns a catalyst comprising at least one zeolite with channels with openings defined by a ring having 10 oxygen atoms (10 MI), at least one zeolite with at least channels or side pockets with openings defined by a ring having 12 oxygen atoms (12 MI), at least one metal selected from the group constituted by group IIIA and VIIB metals and at least one porous mineral matrix. The catalyst of the present invention is free from any group VIII metal.

Zeolites are defined in the "Atlas of Zeolite Structure Types", W M Meier, D H Olson and Ch Baerlocher, 5th revised edition, 2001, Elsevier, to which the present application also makes reference. Zeolites are classified therein by the size of their pore or channel openings. In accordance with the invention, at least one zeolite comprised in the catalyst of the invention has pores or channels with openings defined by a ring having 10 oxygen atoms (10 MI) and at least one zeolite comprised in the catalyst of the invention has at least channels or side pockets with openings defined by a ring having 12 oxygen atoms (12 MI). In accordance with the invention, the channels of the zeolite with a 10 MI opening, hereinafter termed 10 MI zeolite, are principal channels which open directly to the exterior of said zeolite. The zeolite having an opening with at least 12 MI, hereinafter termed the zeolite with at least 12 MI, has at least either 12 MI principal channels opening directly to the exterior of said zeolite or secondary 12 MI channels which are accessible only via the principal channels with an opening other than 12 MI, or side pockets with openings defined by a ring of 12 oxygen atoms. The 10 MI and at least 12 MI zeolites present in the catalyst of the invention comprise silicon and at least one element T selected from the group formed by aluminium, iron, gallium and boron, preferably aluminium. Preferably, they are practically completely in the acid form.

The 10 MI zeolite present in the catalyst of the invention is characterized by a Si/Al ratio in the range 2 to 250, preferably in the range 5 to 150 and more preferably in the range 10 to 80. The sodium content is less than 0.2% by weight, preferably less than 0.1% by weight and more preferably less than 0.05% by weight with respect to the total dry weight of zeolite. All of the zeolites have channels with openings defined by a ring of 10 oxygen atoms (10 MI) and known in the prior art as being suitable for use in the present catalyst. Preferred 10 MI zeolites are selected from ZSM-5, IM-5 and ZSM-22 zeolites. Said zeolites and their preparation mode are well known to the skilled person.

The zeolite with at least 12 MI present in the catalyst of the invention is characterized by a Si/Al ratio in the range 2 to 250, preferably in the range 5 to 150 and more preferably in the range 10 to 80. The sodium content is less than 0.2% by weight, preferably less than 0.1% by weight and more preferably less than 0.05% by weight with respect to the total dry weight of zeolite. All of the zeolites have at least channels (principal or secondary) or side pockets with openings defined by a ring of 12 oxygen atoms (12 MI) and which are known in the prior art as being suitable for use in a catalyst of the present invention. Preferred zeolites with at least 12 MI are selected from beta, Y, mordenite, NU-87, ITQ-23, EU-1 and boggsite zeolites. NU-87 zeolite, with structure type NES, has 10 MI principal channels and also 12 MI secondary channels which are accessible from the 10 MI channels, as described in the book "Synthesis of microporous materials", vol 1, Eds M L Occelli and H E Robson, chapter 24 (Casci J L et al). Boggsite has 10 MI and 12 MI principal channels. EU-1 zeolite has 10 MI principal channels and 12 MI side pockets. Those zeolites and their preparation mode are well known to the skilled person.

The Si/Al ratios of the zeolites described above are those obtained at the end of synthesis of said zeolites or obtained after post-synthesis dealumination treatments which are well known to the skilled person, non exhaustive examples of which are hydrothermal treatments which may or may not be followed by acid attack, or direct acid attack with solutions of mineral or organic acids.

The overall Si/Al ratio of the 10 MI and at least 12 MI zeolites in the composition of the catalyst of the invention and the chemical compositions of the samples are determined by X ray fluorescence and atomic absorption.

The 10 MI zeolites and at least 12 MI zeolites in the composition of the catalyst of the invention can be calcined and exchanged with at least one treatment using a solution of at least one ammonium salt to obtain the ammonium form of the zeolites which, once calcined, produce the hydrogen form of said zeolites.

The 10 MI and at least 12 MI zeolites in the composition of the catalyst of the invention are at least partially, preferably practically completely, in the acid form, i.e. in the hydrogen form ($H^+$). The Na/T atomic ratio is generally less than 10% and preferably less than 5%; more preferably, it is less than 1%.

Said catalyst also comprises at least one metal selected from the group constituted by group IIIA and VIIB metals, preferably in an amount in the range 0.01% to 5% by weight with respect to the total catalyst weight. Rhenium is the preferred group VIIB metal. Gallium is the preferred group IIIA metal. The catalyst of the invention optionally further comprises at least one metal selected from the group constituted by group IVA and VIB metals, preferably in an amount in the range 0.01% to 5%, more preferably in the range. 0.5% to 3% by weight with respect to the total catalyst weight. Tin is the preferred group IVA metal. Molybdenum is the preferred group VIB metal. The catalyst of the present invention is free from any group VIII metal.

The porous mineral matrix, present in an amount in the range 5% to 95%, preferably in the range 10% to 90%, more preferably in the range 15% to 85% and still more preferably in the range 20% to 80% by weight with respect to the total catalyst weight, is generally selected from elements from the group formed by clays (for example natural clays such as kaolin or bentonite), magnesia, aluminas, silicas, titanium oxide, boron oxide, zirconia, aluminium phosphates, titanium phosphates, zirconium phosphates, silica-aluminas and coal, preferably from elements from the group formed by aluminas and clays, more preferably from aluminas.

The 10 MI and at least 12 MI zeolites are recorded in the zeolites atlas and are synthesized using methods described in the references described in that work ("Atlas of Zeolite Structure Types", W M Meier, D H Olson and Ch Baerlocher, 5$^{th}$ revised edition, 2001) or by any other method described in the literature available to the skilled person. Any commercial zeolite can also be used to obtain the catalyst of the invention.

In a first variation for preparing the catalyst of the invention, prior to forming, at least one of the zeolites described above and included in said catalyst is deposited with at least one metal selected from the group constituted by group IIIA and VIIB metals. Preferably, at least the 10 MI zeolite is deposited with at least one metal selected from the group constituted by group IIIA and VIIB metals. It is also possible for the 10 MI zeolite to be deposited with a metal selected from the group constituted by group IIIA and VIIB metals and for the zeolite with at least 12 MI to be deposited with another metal selected from the group constituted by group IIIA and VIIB metals. Advantageously, when the catalyst of the invention comprises at least one metal selected from the group constituted by group IIIA and VIIB metals and at least one metal selected from the group constituted by group IVA and VIB metals, the 10 MI zeolite is deposited with a metal selected from the group constituted by group IIIA and VIIB metals and the zeolite with at least 12 MI is deposited with a metal selected from the group constituted by group IVA and VIB metals. The zeolites, charged with metals, are then mixed. Said zeolites, which are in powder form, are mixed using powder mixing techniques which are known to the skilled person.

Once the powdered metal-charged zeolites have been mixed, the mixture is formed using any technique known to the skilled person. In particular, it can be mixed with a porous mineral matrix, generally amorphous, for example a moist alumina gel powder. The mixture is then formed, for example by extrusion through a die.

Forming can be carried out with matrices other than alumina, examples being magnesia, amorphous silica-aluminas, natural clays (kaolin, bentonite, sepiolite, attapulgite), silica, titanium oxide, boron oxide, zirconia, aluminium phosphates, titanium phosphates, zirconium phosphates, coal and mixtures thereof. Preferably, matrices containing alumina in all forms known to the skilled person are used, more preferably aluminas, for example gamma alumina. Advantageously, mixtures of alumina and silica, or mixtures of alumina and silica-alumina can also be used. Other extrusion techniques such as pelletization or bowl granulation can be used.

After forming, the product obtained undergoes a drying step then a calcining step.

In a second variation for the preparation of the catalyst of the invention, at least one metal selected from the group constituted by group IIIA and VIIB metals and optionally at least one metal selected from the group constituted by group IVA and VIB metals is (are) deposited on the support after forming the metal-free zeolites, using any process known to the skilled person to allow metal to be deposited on the zeolites. The term "support" means the mixture of zeolites (metal-free) with at least one porous mineral matrix after forming, drying and calcining.

The support for the catalyst of the present invention generally has the following amounts of matrix and zeolites:

5% to 95% by weight, preferably 10% to 90% by weight, more preferably 15% to 85% by weight and still more preferably 20% to 80% by weight of zeolites such that at least one zeolite is selected from 10 MI zeolites and at least one zeolite is selected from zeolites with at least 12 MI;

5% to 95%, preferably 10% to 90%, more preferably 15% to 85% and still more preferably 20% to 80% by weight of at least one porous amorphous or low crystallinity oxide type mineral matrix.

In order to deposit metal on the zeolites of the first and second variation in the preparation of the catalyst of the invention, competitive cation exchange can be used, wherein the competitor is preferably ammonium nitrate, the competition ratio being at least about 20 and advantageously about 30 to 200. Dry impregnation or co-precipitation can also be used.

The sources of group VIIB metals which can be used are also well known to the skilled person. In the case of rhenium, an ammonium perrhenate $(NH_4)ReO_4$ complex or perrhenic acid is normally used. The sources of group IIIA metals which can be used are also well known to the skilled person. In the case of gallium, gallium nitrate $Ga(NO_3)_3$ is preferred. The sources of group VIB metals which can be used are also well known to the skilled person. In the case of molybdenum, molybdic acids and their salts can be used, in particular ammonium salts such as ammonium molybdate, ammonium heptamolybdate and phosphomolybdic acid. Preferably, ammonium heptamolybdate $(NH_4)_6Mo_7O_{24}$ is used. The group IIIA and VIIB metal or metals and optional group IVA and VIB metal or metals is generally followed by calcining in air or oxygen, usually between 300° C. and 600° C. for 0.5 to 10 hours, preferably between 350° C. and 550° C. for 1 to 4 hours. Reduction in hydrogen can then be carried out, generally at a temperature in the range 300° C. to 600° C. for 1 to 10 hours, preferably in the range 350° C. to 550° C. for 2 to 5 hours.

It is also possible to deposit the metal not directly on the zeolites, but on the porous mineral matrix (for example the alumina binder) of the support, before or after the forming step, by carrying out an anion exchange step. An example which can be cited in the case of depositing rhenium is the use of perrhenic acid $HReO_4$ for rhenium. In general, after depositing the metal, the catalyst undergoes calcining then is reduced in hydrogen, as indicated above.

In a further variation of the invention, each zeolite is independently formed with a binder. The zeolite mixture can be produced after forming (extrudates or grains). The metals are deposited before or after mixing the formed zeolites, preferably before. A different metal can then be deposited on the two formed zeolites. Preferably, the molybdenum is deposited on one of the two zeolites, preferably on the zeolite with at least 12 MR.

When the catalyst contains a plurality of metals, these latter may be introduced either all in the same manner or using different techniques, before or after forming depending on the catalyst preparation variation employed and in any order. When the technique used is ion exchange, several successive exchanges may be necessary to introduce the required quantities of metals.

Regardless of the variation used in preparing the catalyst of the invention, after calcining said catalyst, hydrogen reduction can be carried out, generally at a temperature in the range 300° C. to 600° C., preferably in the range 350° C. to 550° C., for a period in the range 1 t preferably in the range 2 to 5 hours. Said reduction can be carried out ex situ or in situ, relative to the location at which said catalyst is used in a given reactor.

The distribution between the two zeolites of each of the groups defined above is such that the amount of zeolite(s) selected from the group formed by 10 MI zeolites is from 1% to 99%, preferably 5% to 95% and more preferably 10% to 90% as a percentage relative to the total of the zeolites introduced into the catalyst. Similarly, the amount of zeolite with at least 12 MI is 1% to 99%, preferably 5% to 95% and more preferably 10% to 90%, as a percentage relative to the total of the zeolites introduced into the catalyst.

The catalyst of the present invention is formed into grains with different shapes and dimensions. It is generally used in the form of cylindrical extrudates or polylobed extrudates such as bilobes, trilobes, polylobes with a straight or twisted form, but may also be manufactured and employed as crushed powders, tablets, rings, beads, or wheels. Highly preferably, the catalyst of the invention comprises at least one metal selected from the group constituted by metals from group IIIA and VIIB on the 10 MI zeolite.

The catalyst of the present invention may also contain sulphur. In this case, the sulphur is introduced onto the formed calcined catalyst containing the element or elements cited above, either in situ before the catalytic reaction or ex situ. Sulphurization is carried out using any sulphurizing agent that is well known to the skilled person, such as dimethyl disulphide or hydrogen sulphide. Optional sulphurization is carried out after reduction. In the case of in situ sulphurization, if the catalyst has not been reduced, reduction is carried out before sulphurization. In the case of ex situ sulphurization, reduction is carried out followed by sulphurization.

The catalyst of the invention is used for hydrocarbon conversion.

In particular, the invention concerns the use of said catalyst in a process for the transalkylation of an alkylaromatic hydrocarbon feed, preferably transalkylation of benzene or toluene and alkylaromatic hydrocarbons which are generally $C_9^+$ (i.e. at least 9 carbon atoms per molecule), with benzene-AC9+ or toluene-AC9+ mixtures (AC9+designates alkylaromatic hydrocarbons comprising at least 9 carbon atoms per molecule), which may contain 1% to 100% AC9+ with respect to the total mixture. Said catalyst has proved highly effective for this use, as it is particularly active, selective and stable, even in the presence of feeds to be treated containing a large quantity of heavy AC9+ aromatics, said heavy aromatics possibly containing a large proportion of AC10+. Thus, AC9+ feeds containing at least 5% and up to 25% by weight and furthermore, even AC10+ can be upgraded. Non exhaustive examples which can be cited are dimethylethylbenzenes, diethylbenzenes, propylethylbenzenes, etc. The use of said catalyst in the transalkylation of heavy alkylaromatics is thus of particular interest.

The operating conditions for said use are generally as follows: a temperature in the range 250° C. to 650° C., preferably in the range 350° C. to 550° C.; a pressure in the range 1 to preferably in the range 2 to 4.5 MPa; a space velocity, expressed in kilograms of feed introduced per kilogram of catalyst per hour, in the range 0.1 to 10 h$^{-1}$ and preferably in the range 0.5 to 4 h$^{-1}$; a mole ratio of hydrogen to hydrocarbons in the range 2 to 20 and preferably in the range 3 to 12 mol/mol.

The following examples illustrate the invention without in any way limiting its scope.

EXAMPLE 1

Preparation of Catalysts Based on 10 MI Zeolites (Comparative), Based on Zeolites with at Least 12 MI (Comparative) and Based on 10 MI Zeolite and Zeolite with at Least 12 MI (In Accordance with the Invention)

The zeolites used to prepare the catalysts of the invention are shown in Table 1 with their composition (Si/Al atomic ratio) and their residual sodium content. The five zeolites concerned were all in the acid form.

The beta, mordenite and ZSM-5 zeolites were all commercial zeolites (PQ).

The NU-87 zeolite was synthesized in accordance with European patent EP-A-0 377 291 or EP-B-0 378 916. It had an overall Si/Al atomic ratio of 17.2, a sodium content of 1256 ppm. This NU-87 zeolite first underwent dry calcining at 550° C. in a stream of air and nitrogen for 6 hours. The solid obtained then underwent ion exchange in a 10N NH$_4$NO$_3$ solution, at about 100° C. for 4 hours. The NU-87 zeolite then underwent treatment with a 7N nitric acid solution at about 100° C. for 5 hours. The volume V of the nitric acid solution used (in ml) was 10 times the weight W of the dry NU-87 zeolite (V/W=10). This treatment using a 7N nitric acid solution was carried out a second time under the same operating conditions.

At the end of these treatments, the zeolite obtained was in its H form and had an overall Si/Al atomic ratio of 33.3 and a Na content of 10 ppm.

The IM-5 zeolite was synthesized according to Example 1 of FR-A-2 754 809 or U.S. Pat. No. 6,136,290.

TABLE 1

| 10 MR zeolites and zeolites with at least 12 MR | | | |
|---|---|---|---|
| Zeolites | Si/Al (XRF) | Na (ppm) | Type |
| Beta | 12.5 | 87 | 12 MR |
| ZSM-5 | 17.5 | 132 | 10 MR |
| MOR | 10 | 109 | 12 MR |
| IM-5 | 12 | 84 | 10 MR |
| NU-87 | 33.3 | 10 | 10 & 12 MR |

The zeolites were then formed by extrusion with an alumina gel to obtain, after drying and calcining in dry air, a support which contained 80% by weight of zeolite and 20% by weight of alumina. The zeolitic portion of the support was constituted by a zeolite alone (not in accordance with the invention) or a mechanical mixture of two different zeolites carried out before forming (in accordance with the invention).

To prepare catalysts A to N, the zeolitic support comprising one zeolite or a mixture of two different zeolites underwent dry impregnation using a solution of metallic precursor (ammonium perrhenate for rhenium, ammonium heptamolybdate for molybdenum, gallium nitrate for gallium, nickel nitrate for nickel) to deposit the required percentage of metal. The moist solid was then dried at 120° C. for 12 hours and calcined in a flow of dry air at a temperature of 500° C. for one hour. The composition of the catalysts obtained is shown in Table 2.

For catalysts O and P, the extruded support containing beta zeolite with a deposit of molybdenum (catalyst M) or gallium (catalyst N) was mechanically mixed with the extruded support containing ZSM-5 zeolite with a deposit of rhenium (catalyst B).

TABLE 2

Catalysts containing either a 10 MR zeolite (not in accordance with the invention) or a zeolite with at least 12 MR (not in accordance with the invention) or a 10 MR zeolite and a zeolite with at least 12 MR (in accordance with the invention)

| Catalyst | % Al$_2$O$_3$ | Zeolite(s) | Zeolite ratio | % metal |
|---|---|---|---|---|
| A | 20 | Beta | 100 | 0.5% Re |
| B | 20 | ZSM-5 | 100 | 0.5% re |
| C | 20 | MOR | 100 | 0.5% Re |
| D | 20 | IM-5 | 100 | 0.25% Re |
| E | 20 | NU-87 | 100 | 0.25% Re |
| F | 20 | Beta + ZSM-5 | 50/50 | 0.5% re |
| G | 20 | MOR + ZSM-5 | 50/50 | 0.5% Re |
| H | 20 | NU-87 + ZSM-5 | 50/50 | 0.25% Re |
| I | 20 | Beta + IM-5 | 50/50 | 0.25% Re |
| J | 20 | NU-87 + IM-5 | 34/66 | 0.25% Re |
| K | 20 | NU-87 + IM-5 | 66/34 | 0.25% Re |
| M | 20 | Beta | 100 | 1% Mo |
| N | 20 | Beta | 100 | 1% Ga |
| O | 20 | Beta + ZSM-5 | 50/50 | 0.5% Mo/beta 0.25% Re/ZSM-5 |
| P | 20 | Beta + ZSM-5 | 50/50 | 0.5% Ga/beta 0.25% Re/ZSM-5 |

EXAMPLE 2

Catalytic Performances of Catalysts Based on 10 MI Zeolites (Comparative), Based on Zeolites with at Least 12 MI (Comparative) and Based on a 10 MI Zeolite and a Zeolite with at Least 12 MI (In Accordance with the Invention)

The catalysts were initially reduced in hydrogen at 450° C. for 2 h.

The catalytic tests were carried out under the following operating conditions:

temperature: 400° C.;

total pressure: 25 bar;

H$_2$/HC=8.5 mol/mol;

WHSV=4 h$^{-1}$ (mass of feed per gram of catalyst per hour).

The feed was constituted by 50% of toluene, 16% of ethyltoluene, 28% of trimethylbenzene and 6% of aromatics containing at least 10 carbon atoms.

| Catalysts | A | B | C | D | E |
|---|---|---|---|---|---|
| Overall conversion (%) | 58.9 | 40.1 | 56.9 | 45.8 | 50.3 |
| Yields (wt %) | | | | | |
| Lights (C$_1$-C$_4$) | 16.1 | 9.5 | 9.5 | 4.6 | 4.6 |
| Benzene + xylenes | 33.6 | 23.8 | 38.1 | 33.1 | 37.8 |
| Ethylbenzene | 1.6 | 0.1 | 0.7 | 0.5 | 1.0 |
| Heavies | 5.6 | 2 | 3.1 | 4.3 | 4.3 |

-continued

| Catalysts | F | G | H | I | J | K |
|---|---|---|---|---|---|---|
| Overall conversion (%) | 56.0 | 51.9 | 52.3 | 51.1 | 50.9 | 52.0 |
| Yields (wt %) | | | | | | |
| Lights ($C_1$-$C_4$) | 7.5 | 6.6 | 5.6 | 7.3 | 5.1 | 4.6 |
| Benzene + xylenes | 41.4 | 39.4 | 39.2 | 37.0 | 38.7 | 39.5 |
| Ethylbenzene | 0.1 | 0.2 | 0.2 | 0.5 | 0.4 | 0.5 |
| Heavies | 2.5 | 2.5 | 3.2 | 2.7 | 3.2 | 3.7 |

| Catalysts | M | N | O | P |
|---|---|---|---|---|
| Overall conversion (%) | 57.6 | 56.2 | 57.3 | 57.1 |
| Yields (wt %) | | | | |
| Lights ($C_1$-$C_4$) | 13.3 | 14.1 | 8.2 | 7.8 |
| Benzene + xylenes | 34.5 | 34.8 | 41.8 | 40.9 |
| Ethylbenzene | 1.3 | 1.2 | 0.3 | 0.2 |
| Heavies | 6.1 | 7.3 | 3.6 | 4.3 |

The use of catalysts containing mixtures constituted by at least one 10 MI zeolite and at least one zeolite with at least 12 MI in the context of the present invention can increase the yield of xylenes and benzene, which are the target products for the transalkylation reaction as they can be readily upgradeable.

The invention claimed is:

1. A catalyst comprising at least one zeolite with channels with openings defined by a ring having 10 oxygen atoms, at least one zeolite with at least channels or side pockets with openings defined by a ring having 12 oxygen atoms, at least one metal from one or both of groups IIIA and VIIB metals, and at least one porous mineral matrix, said catalyst being free from any group VIII metal.

2. A catalyst according to claim 1, in which the at least one zeolite with channels with openings defined by a ring of 10 oxygen atoms comprises a ZSM-5, IM-5 or a ZSM-22 zeolite.

3. A catalyst according to claim 1, in which the zeolite with at least channels or side pockets with openings defined by a 12 oxygen atom ring comprises a Beta, Y, mordenite, NU-87, EU-1 or boggsite zeolites.

4. A catalyst according to claim 1, further comprising at least one metal from group IVA or VIB metals.

5. A catalyst according to claim 1 comprising rhenium.

6. A catalyst according to claim 1 comprising gallium.

7. A catalyst according to claim 1 comprising molybdenum.

8. A catalyst according to claim 1, comprising sulphur.

9. In a catalytic process comprising catalytically transalkylating an alkylaromatic hydrocarbon feed, the improvement wherein the catalyst is according to claim 1.

10. A process according to claim 9, comprising transalkylating at least one of benzene or toluene or alkylaromatic hydrocarbons containing at least 9 carbon atoms per molecule.

11. A process according to claim 10, comprising transalkylating an aromatic feed containing at least 5% by weight of aromatics containing at least 10 carbon atoms.

12. A process according to claim 9 conducted at a temperature in the range of 250° C. to 650° C., a pressure in the range of 1 to 6 MPa, a supply space velocity, expressed in kilograms of feed introduced per kilogram of catalyst per hour, in the range of 0.1 to 10 $h^{-1}$, and a mole ratio of hydrogen to hydrocarbons in the range of 2 to 20.

13. A catalyst according to claim 2, in which the zeolite with at least channels or side pockets with openings defined by a 12 oxygen atom ring comprises a Beta, Y, mordenite, NU-87, EU-1 or boggsite zeolites.

14. A catalyst according to claim 5 comprising molybdenum.

15. A catalyst according to claim 6 comprising molybdenum.

16. A catalyst according to claim 3 comprising molybdenum and at least one of gallium and rhenium.

17. A catalyst according to claim 16 comprising molybdenum.

18. A catalyst according to claim 1 comprising a Beta zeolite and a ZSM-5 zeolite and a gallium or rhenium metal.

19. In a catalytic process comprising catalytically transalkylating an alkylaromatic hydrocarbon feed, the improvement wherein the catalyst is according to claim 16.

20. In a catalytic process comprising catalytically transalkylating an alkylaromatic hydrocarbon feed, the improvement wherein the catalyst is according to claim 18.

* * * * *